United States Patent [19]
Colbert

[11] Patent Number: 5,478,335
[45] Date of Patent: Dec. 26, 1995

[54] HYGIENIC ABSORBENT DEVICES

[75] Inventor: Adrian J. Colbert, Sutton Coldfield, United Kingdom

[73] Assignee: Smith & Nephew plc, United Kingdom

[21] Appl. No.: 859,406

[22] PCT Filed: Apr. 16, 1992

[86] PCT No.: PCT/GB92/00707

§ 371 Date: May 27, 1992

§ 102(e) Date: May 27, 1992

[87] PCT Pub. No.: WO92/18078

PCT Pub. Date: Oct. 29, 1992

[30] Foreign Application Priority Data

Apr. 18, 1991 [GB] United Kingdom ............ 9108347
May 21, 1991 [GB] United Kingdom ............ 9110981
Jul. 13, 1991 [GB] United Kingdom ............ 9115146
Jul. 18, 1991 [GB] United Kingdom ............ 9115542

[51] Int. Cl.⁶ .................................. A61F 13/20
[52] U.S. Cl. ..................... 604/383; 604/370; 604/366
[58] Field of Search .......................... 604/358, 368, 604/378, 381–384, 372, 365, 366, 385.1

[56] References Cited

U.S. PATENT DOCUMENTS

| | | | |
|---|---|---|---|
| 3,460,536 | 8/1969 | Champaigne | 604/378 |
| 3,994,299 | 11/1976 | Karami | 604/378 |
| 4,173,046 | 11/1979 | Gallagher | 604/378 |
| 4,323,068 | 4/1982 | Aziz | 604/378 |
| 4,323,069 | 4/1982 | Ahr et al. | 604/372 |
| 4,519,798 | 5/1985 | Dinius . | |
| 4,780,352 | 10/1988 | Palumbo | 604/378 |
| 4,798,603 | 1/1989 | Meyer et al. | 604/378 |
| 5,047,023 | 9/1991 | Berg | 604/368 |
| 5,079,081 | 1/1992 | Lai | 604/381 |

FOREIGN PATENT DOCUMENTS

| | | |
|---|---|---|
| 0178108 | 4/1986 | European Pat. Off. . |
| 0040084 | 11/1991 | European Pat. Off. . |
| 1610508 | 5/1971 | Germany . |
| 2225724 | 5/1990 | United Kingdom . |

Primary Examiner—Randall L. Green
Assistant Examiner—Rob Clarke
Attorney, Agent, or Firm—Rosenman & Colin

[57] ABSTRACT

An absorbent device having low fluid wet-back and good surface cleanliness and resistance to staining is provided which comprises an absorbent core, a cover sheet on a body facing side thereof and an intermediate layer between the cover sheet and the core wherein the cover sheet comprises an apertured polymer film for example a flexible polymer net and the intermediate layer comprises a planar apertured polymer film for example a flexible polymer net.

12 Claims, 2 Drawing Sheets

HYGIENIC ABSORBENT DEVICES

The present invention relates to hygienic absorbent devices and in particular relates to devices in the form of sanitary napkins, diapers, incontinence pads and the like.

Conventional absorbent devices such as sanitary napkins or towels, diapers, incontinence pads and the like normally comprise an absorbent core and a liquid pervious cover sheet over the body facing side thereof. The cover sheet will make direct contact with the user's skin in use. Any body fluids such as blood, urine and the like will contact the cover sheet before being transmitted therethrough to the absorbent core. It is a common problem with hygienic absorbent devices that in use if pressure is exerted on the device absorbed fluid may be squeezed out of the core and be returned back to the surface of the device thereby re-wetting the cover sheet and hence also the skin of the user. This fluid wet-back of conventional absorbent devices is undesirable because it can render the devices uncomfortable to wear and also cause skin irritation and rashes if contact between the body fluid and the skin in prolonged. Some success in overcoming this fluid wet-back problem has been obtained by interposing a contoured or deformed intermediate layer between the cover sheet and absorbent core. Such layers, however, have a fairly complex construction and also require special deforming or contouring apparatus for their manufacture.

In European Patent Specification No. 0178108 there is described a hygienic absorbent pad comprising an absorbent layer, a cover layer and an intermediate layer which is an embossed plastics net. The use of embossed plastics nets having a well defined three dimensional character was proposed to provide good separation of the cover layer from the absorbent layer, serves to inhibit fluid wet-back. However not only does the imposition of a three dimensional character on the intermediate layer, increase the complexity and cost of the product it also may make the product more bulky and less deformable and can cause a rough feeling. However EP-A-0176108 taught that it was necessary to use such corrugated materials to achieve low wet-back and did not suggest that effectively flat materials could be employed.

U.K. Patent Specification No. 2225724 discloses an absorbent device comprising an absorbent core, a cover layer and an intermediate layer comprising an apertured, contoured film of an elastomeric polymer material. The production of such contoured apertured intermediate layer suffers from the drawbacks as described above but GB-A-225724 taught that the use of such corrugated materials were necessary to achieve low wet-back and did not suggest that effectively flat materials could be employed.

It is also known that menstrual fluid may be retained on the surface of a cover layer and cause unsightly staining. Entrappment of fluid in the cover sheet interstices, for example between the fibers of a non-woven cover sheet may also cause discomfort for the user.

The problems of surface cleanliness and fluid wet-back have been addressed in European Patent Specification No. 0040084. This reference teaches an absorbent article including an absorbent core which has an overlaying liquid pervious topsheet with a layer of fibers affixed to the non-body facing side and a layer of an embossed plastics film provided with a multiplicity of tapered capilliaries located between the fibrous layer and the core. The layer of fibers affixed to the inner surface of the top, is necessary to improve strike through or penetration of fluid through the top sheet. Thus the absorbent devices of EP0040084 require the use of complex layers and require specialised processing techniques for their manufacture.

The present invention seeks to ameliorate the disadvantages of the prior art in that the use of contoured, bulky intermediate layers or complex composite layers to assist fluid penetration is avoided by the use of two overlying and adjacent apertured polymer films to cover the absorbent core of an absorbent device such as a disposable napkin. In this way not only are the absorbent devices of the invention of a simpler construction compared with the prior art but also combine low wet-back properties with a high degree of surface cleanliness. It is particularly surprising that this can be achieved employing a planar film which thereby avoids the disadvantage of corrugated materials of the type described in EP-A-0178108 or GB-A-2225724.

Accordingly, the present invention provides an absorbent device having low fluid wet-back comprising an absorbent core, a cover sheet over a body facing side thereof and an intermediate layer between the cover sheet and the core wherein the cover sheet comprises an apertured polymer film and the intermediate layer comprises a planar apertured polymer film.

The present invention further provides an absorbent device having low fluid wet-back and a high relative brightness comprising an absorbent core, a body contacting cover sheet on a body facing side of the core, and an intermediate sheet between the core and the cover sheet wherein the cover sheet comprises an apertured polymer film and the intermediate sheet comprises a planar apertured polymer film.

Also in accordance with the invention there is provided a method of producing absorbent devices having low fluid wet-back comprising covering a body facing surface of an absorbent core with a cover sheet and an intermediate layer between the cover sheet and the core wherein the cover sheet comprises an apertured polymer film and the intermediate layer comprises a planar apertured polymer film.

The planar apertured films employed in the present invention are substantially flat. The films may contain some surface deformation caused for example during the film forming or aperturing process or for cosmetic decoration. However any surface deformation should be great enough to change the wet-back properties of the film layer from that of a flat film.

The hygienic absorbent device of the invention can be a sanitary towel, diaper, dressings, incontinence pad or the like absorbent pad. Preferably the device is a sanitary towel. It is in sanitary towels that the benefits of the invention are greatest.

The apertures in the apertured polymer films are holes. Such apertures therefore do not include the interstices between the fibers a non-woven fabric cover sheet (that is a sheet of entangled fibers or the like).

The apertures in the polymer are provided all over at least the operative part of the device, e.g. at least in the region which overlies the body facing surface of an absorbent device. Aptly apertures are provided over the entire surface of the cover or intermediate layer.

Suitably an apertured polymer film may be a polymer net. A polymer net as used herein is a polymer sheet having apertures defined by integral strands and junctures formed from the polymer material. The term 'apertured film' as used herein will be understood to include such polymer nets.

The absorptive devices of the invention have low fluid wet-back values. The fluid wet-back is the amount of a test fluid which strikes back through to the body contacting surface of the device when the device is subjected to a standard load and the test for determining wet-back is hereinafter described.

Devices of the present invention aptly have a fluid wet-back value of less than 0.5 g, suitably not greater than 0.2 g and preferably less than 0.1 g.

The absorbent devices of the present invention are further characterised as possessing good surface cleanliness of the body contacting layer and a high resistance to staining by body fluids such as menses. The surface cleanliness properties are defined by the results of a relative optical brightness test which is described hereinafter and in which the optical brightness of a stained area of the body contacting surface of the device is compared with that of an unstained area of the body contacting surface. The closer that the relative optical brightness value is to unity the more stain resistant and clean-looking is the surface of the body contacting layer. The absorbent devices of the present invention will aptly have a relative optical brightness value of greater than 0.65 and suitably greater than 0.75. Preferred devices of the invention will have a relative optical brightness value of at least 0.80. These desirable properties are best achieved by using two planar layers of apertured film, particularly by using two layers of planar net.

The absorbent devices of the invention consist of two or more apertured films overlying the absorbent core. The absorbent device will therefore comprise a first apertured polymer film overlying a second film which is a planar apertured film and which is between the first film and the absorbent core. For economy of materials it is preferred to employ only two such layers. If desired more than two apertured films for the body contacting layer may be used. However, this is not normally necessary or desirable except that the use of three film layers may be preferred for absorptive devices which are not generally planar. The use of three or more film layers may be employed for use in 'shaped' sanitary towels (that is sanitary towels shaped to fit the female anatomy). Aptly, at least two of the apertured films may be planar apertured films. In another embodiment of this aspect of the invention, the body contacting layer may comprise an apertured polymer film, overlying a second film which is a planar apertured polymer film and wherein another liquid pervious layer such as a third apertured polymer film, e.g. a polymer net or perforated film or non-woven fabric lies between that liquid pervious layer and the core.

In accordance with a preferred embodiment, the present invention provides a low wet-back absorptive device having an absorbent pad covered on one surface by an apertured body facing layer comprising a layer of two flexible polymer nets.

Each of the apertured films employed in the device of the invention can have an open area which is suitably at least 25%, favourably at least 30% and preferably at least 35% of the area of the total area film. Similarly, the apertured film can have an open area which is suitably not greater than 90%, favourably not greater than 70% and preferably not greater than 60% and most preferably not greater than 45% of the area of the total areas of the film.

Aptly a film comprising the cover sheet has an open area greater than the open area of the film comprising an intermediate layer.

The intermediate layers for example the second and subsequent apertured polymer films can have an open area which is suitably at least 5%, favourably at least 10% and preferably at least 15% of the area of the cover layer. Similarly the intermediate layer can have an open area which is suitably not greater than 25%, favourably not greater than 23% and preferably not greater than 21% of the area of the cover layer.

The largest dimension of the apertures in the cover layer of the device of the invention can suitably be at least 0.1 mm and can preferably be at least 0.4 mm in size. Similarly, the largest aperture dimension can suitably be not greater than 2 mm in size and can preferably be not greater than 1.5 mm in size.

The apertures in an intermediate layer can aptly be the same size as those of the first apertured film. They may suitably have a largest dimension size of at least 0.1 mm and can preferably be at least 0.2 mm in size. However the largest dimension size of the apertures in the apertured film need not be greater than 1.0 mm in size and can preferably be not greater than 0.8 mm in size.

The apertures in each of the films of the component layers may have a symmetrical shape such as a square, diamond, circular or triangular shape or an unsymmetrical shape for example, an elongate shape such as rectangular or oval shape.

The size of apertures as hereinabove mentioned therefore refer to maximum size dimension of the apertures.

The apertures in the films component layers can be formed by any suitable conventional perforating process. Such processes include mechanical perforation using needles or punches, hot melt perforation of selected areas using for example heated protruberances such as heated needles or embossed rollers or hot fluid such as flame or hot gases. Nets may be formed by stretching such perforated films or by stretching a film or sheet embossed with thinner areas.

Favoured apertured polymer films in the form of polymer nets comprise an elastomeric polymer and in particular a thermoplastic elastomeric polymer.

Such nets of elastomeric polymer can impart 'softness' to the surface of the device of the invention. Aptly the cover layer is comprised of such a polymer net.

Suitable thermoplastic elastomeric polymers include polyether ester and polyether-polyamide block copolymers, polyurethanes, styrene-butadiene and styrene-isoprene block copolymers, polyisobutadiene and ethylene-vinyl acetate copolymers.

Nets for use in the invention may comprise a blend of elastomeric polymer such as ethylene vinyl acetate copolymer with a compatible polymer or an incompatible polymer such as polyolefine, for example low density polyethylene or polystyrene.

Suitable nets for use in the invention which comprise a blend of ethylene vinyl acetate and an incompatible polymer are disclosed in European Patent No. 141592.

A favoured material for the nets used in the invention is a blend of an ethylene-vinyl acetate copolymers (EVA) preferably in amounts of at least 10% by weight and an incompatible polymer preferably in amounts of at least 10% by weight such as a polyolefin. Examples of suitable polyolefins include polystyrene and polyethylenes such as low density and linear low density polyethylenes. A particularly preferred material is a blend of from 10 to 90 parts by weight of ethylene-vinyl acetate copolymer and 90 to 10 parts by weight of polyolefin and more preferably 20 to 80 parts by weight of ethylene-vinyl acetate copolymer and 80 to 20 parts by weight of polystyrene. Typical examples of such a blend comprises a blend of 40 parts ethylene-vinyl acetate copolymer and 60 parts high impact polystyrene, or a blend about 25 parts ethylene-vinyl acetate copolymer, about 13 parts high impact polystyrene and about 60 parts linear low density polyethylene.

Other nets for use in the invention, and which may aptly be employed for an intermediate layer may comprise a blend of a polyolefine and an incompatible polymer. Such nets are described in U.K. Pat. Nos. 914489, 1055963, 1110057 and 1548865. Suitable nets of this type are formed from a blend of polyethylene and high impact polystyrene. Such are available from Smith & Nephew Plastics Ltd. under the Trade Mark Net 909 grades A4, A7, H6C and DHM.

A net for use in the device of the invention can have a weight per unit area which is suitably at least 5 $gm^{-2}$ and which is preferably at least 10 $gm^{-2}$. Similarly the net can have weight per unit area which is suitably not greater than 50 $gm^{-2}$ and which is preferably not greater than 40 $gm^{-2}$.

Such a net can have a thickness which is suitably at least 25 μm and which is preferably at least 50 μm. Similarly the net can have thickness which is suitably not greater than 300 μm and which is preferably not greater than 150 μm. The thickness of the net is determined by measuring across the thickest part of the net, i.e. the strand or boss.

High density polyethylene nets aptly have a thickness of from 100 to 150 μm whereas softer nets such as those made from high density polystyrene and EVA polymer blends may have thicknesses of from 75 to 100 μm. Preferred nets for use in the invention have weight per unit area of 10 to 40 $gm^{-2}$ and a thickness of 50 to 150 μm.

Apt nets comprising high density polystyrene and EVA are known as Net 2000 Ref. Nos. LET6H27, LETH35, LE6H30, LE7H20, LE7625 and LE7630 marketed by Smith & Nephew Plastics Ltd.

Other planar apertured films such as perforated polymer films for use in the invention alone or in addition to net layers can comprise any suitable water insoluble non-toxic pharmaceutical acceptable polymer. Such polymers may be relatively inelastic so that the apertures in the film are not enlarged by stretching of the device caused, for example, by movement of the wearer.

Favoured polymers include polyolefins such as polypropylene or high density polyethylene, polyamides, unplasticised polyvinyl chloride and polyesters such as polyethylene terephthalate.

The apertured film should have a thickness which is sufficient to prevent it tearing but which low enough to render the film flexible.

An apertured film for use in the invention can have a thickness which is suitably at least 6 μm and which is preferably at least 10 μm. Similarly the apertured film can have a thickness which is suitably not greater than 0.075 μm and which is preferably not greater than 50 μm.

Favoured apertured films used in the invention have a thickness of 6 to 50 μm and preferably a thickness of 10 to 30 μm. Apt planar perforated films for use in the invention comprise polyethylene terephthalate have thickness of 10 to 15 μm and have preferably been perforated by flaming. Other perforated films such as those formed from polyethylene, e.g. those known as Breadwrap film reference No. 20/330 available from Bakery Packaging Service Ltd may also be used.

Other forms of apertured polymeric film particularly suitable for use in the component layers of the absorbent devices of the invention comprise generally planar films having apertures formed in small protruberances or debossements formed in the film surface. Such apertured films include those having a construction similar to that described for the top sheets disclosed in U.K. Patent Specification No. 1526778 and similar materials, for example apertured polymeric films such as described in GB-A-1571922, EP-A-18684, EP-A-39973 and EP-A-40447.

Favourably at least one of the apertured film layers contains a surfactant as this results in the best level of desirable properties herein described. This may be in the body contacting layer or in an intermediate layer. More aptly both or each of the component layers will contain a surfactant. This leads to particularly good relative optical brightness values. The presence of the surfactant also serves to increase the transmission of body fluids through the layer.

Preferably the absorbent contacting layer will contain surfactant.

The surfactant may be applied directly onto the surface of the component net or film layer, for example as a layer or coating, or integrated into the film during the production thereof. Aptly the surfactant may be compounded into the component precursors prior to the base film forming and aperturing processes or, alternatively applied during the net forming process, for example by coextruding the surfactant with the film —or film forming components. Suitably a surfactant may be employed in amounts up to 10% by weight of the net or film, more suitably in amounts up to 5% by weight, for example about 1% by weight.

Apt surfactants for use in the present invention include: polymeric additives such as polydimethyl siloxane, mixed polymers such as polydimethylsiloxane-polypropylene glycol, polyethylene glycol terpolymer and block copolymers, such as the ethylene oxide-propylene oxide-propylene glycol condensates sold under the trade name PLURONIC eg. PLURONIC L103; metallic salts of fatty acids such as calcium stearate; fatty esters such as glyceryl monostearate and glycerol stearate; fatty ethers such as polyoxyethylene lauryl ether, sold under the trade name BRIJ 35 and fatty amides such as lauric diethanolamide.

A preferred surfactant for use in the invention is lauric diethanolamide sold under the trade name LANKROSTAT JP.

If necessary the polymer material may include up to 10% of fillers or whitening agents such as titanium dioxide.

The absorbent material used in an absorbent core of the invention can be any of absorbent materials used in conventional hygienic absorbent pads. Suitable absorbent materials include cellulosic fibers such as commercial fluffed wood pulp, cotton fibers, viscose rayon fibers, and super absorbent material such as grafted cellulose and hydrophilic polymers.

The absorbent material however may be blended a minor proportion of hydrophobic fibers such as polyolefine fibers or polyester fibers. The absorbent material in the core can be surrounded or enveloped by a tissue to consolidate the material in the core.

In the absorbent devices of the invention the cover layer will cover at least the effective central area of the body facing side of the core and will normally cover the whole of the body facing side thereof.

In a sanitary towel of the invention it is preferred that at least the cover layer surrounds the absorbent core and extends beyond the ends thereof. Such a cover sheet can be sealed at an overlap at the non-body facing side and also adjacent to the ends thereof so that it forms an envelope around the core.

A hygienic absorbent device of the invention can optionally but preferably have a liquid impermeable barrier such as polymer film for example polyethylene film over the non-body facing side of the core to inhibit leakage of body fluid or exudate through the back or non-body facing side of the device. The liquid impervious barrier layer may also extend around the sides of the absorbent core to inhibit leakage of fluid therefrom. Aptly, where the cover layer is extended to envelope the core, the barrier layer is situated within the envelope.

In a diaper or incontinence device a barrier film and the non-body facing side of the absorbent core can be attached to the cover sheet on the body facing side thereof by means of a peripheral seal formed for example by heat sealing or adhesive to enclose the absorbent core.

Absorbent devices of the invention in particular a sanitary towel may optionally have adhesive for example in the form of strips on the non-body facing surface to allow attachment of the device to a supporting garment.

The apertured layer may cover only the body facing surface of the absorbent. In such embodiments the apertured films may be separate from or attached to a barrier layer which covers the garment facing surface and, preferably, two sides of the core. However, in other embodiments which comprise a cover sheet enclosing or enveloping the absorbent core, the planar apertured films can also surround the absorbent core. An absorbent fleece layer may be inserted between the apertured layer and the absorbent core to further promote absorption of fluid through the film. Optionally or alternatively the net layers may be attached to each other and/or the absorbent core by, for example, a liquid permeable adhesive or by point bonding, e.g. by the use of ultra sound or the thermal energy.

The absorbent devices of the invention may be generally rectangular in shape with a generally flat body facing surface. Preferred forms of generally rectangular absorbent devices have a small caliper, i.e. are thin. Such forms may have caliper or thickness of less than 5 mm. Avantageously, thin devices may be employed with cores containing a super absorber and may be used as a pant liner. Alternatively the absorbent device may have a profiled body facing surface formed by increasing the thickness of the device in certain regions, for example the central region.

One or more of the component layers may be extended beyond the sides of the device to provide wings or flaps which will extend around the crotch of the garment and be adapted to be secured to a non-body contacting surface of the garment for example by adhesive tabs. Alternatively separate wings or tabs, made of suitable material, may be affixed to the absorbent device. The devices of the present invention are particularly useful in this form of 'winged towels'.

The benefit of improved wet-back brought about by the use of apertured polymer films in accordance with the invention may be demonstrated by a comparison between a device of the invention and a similar device having only one layer. This comparison is the relative wet-back value.

Aptly the devices of the invention will have a relative wet-back value of less than half that of a similar device having only one layer of net, when both devices are tested under identical conditions.

The relative wet-back is expressed as follows:

$$\frac{\text{Wet-back of one-layer product}}{\text{Wet-back of device of the invention}}$$

More aptly the devices of the invention will have a relative wet-back value of at least 10, suitably at least 25, preferably at least 50, more preferably at least 100.

The composite film layers used in the invention are capable of providing a device such as a sanitary towel of the invention with relatively low absolute "wet-back" values whilst maintaining adequate fluid absorption rates.

The absolute 'wet-back' (i.e. the fluid wet-back as meant in claims) is the amount of a test fluid which strikes back through to the body contacting surface of the device when the device is subjected to a standard load. The tests for determining the relative and absolute wet-back values are referred to as the Fluid wet Back Tests and are described hereinafter.

The films and nets used in the device of the invention may be planar and therefore much simpler to manufacture than the contoured intermediate layers of prior art devices. Although the net will not normally be contoured the body facing surface may optionally be embossed with a shallow pattern such as repeat flower pattern to provide, for example, a decorative affect.

The invention will now be illustrated with reference to the following drawings in which.

Figure 1:
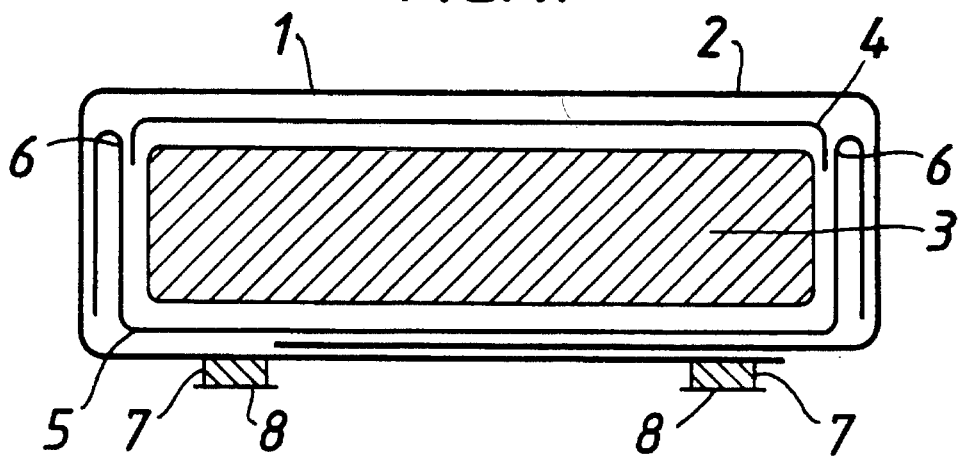
FIG. 1 is a cross-section of a sanitary towel of the invention.

FIG. 1 shows a sanitary towel 1 of the invention having a first net 2 which encloses absorbent core 3 to form an overlap at the non-body facing surface of core 3. Sanitary towel 1 has net 4 covering the body facing surface of core 3 located between net 2 and core 3. Towel 1 as shown in FIG. 1 also has a barrier film 5 covering the non-body facing surface of core 3 with side portions 6 thereof covering the side edges of core 3 to inhibit fluid leakage from towel 1 and adhesive strips 7 covered by release protectors 8 located on an overlap portion of cover sheet 2 to attach towel 1 to a garment.

Figure 2:
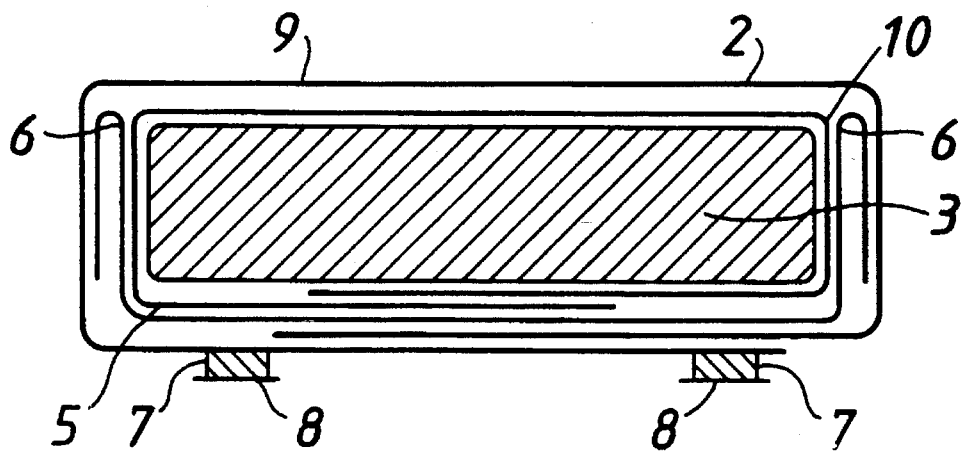
FIG. 2 is a similar cross-section of another sanitary towel of the invention.

FIG. 2 shows another sanitary towel 9 of the invention similar to that of FIG. 1 in which intermediate planar net 10 encloses core 3.

Figure 3:
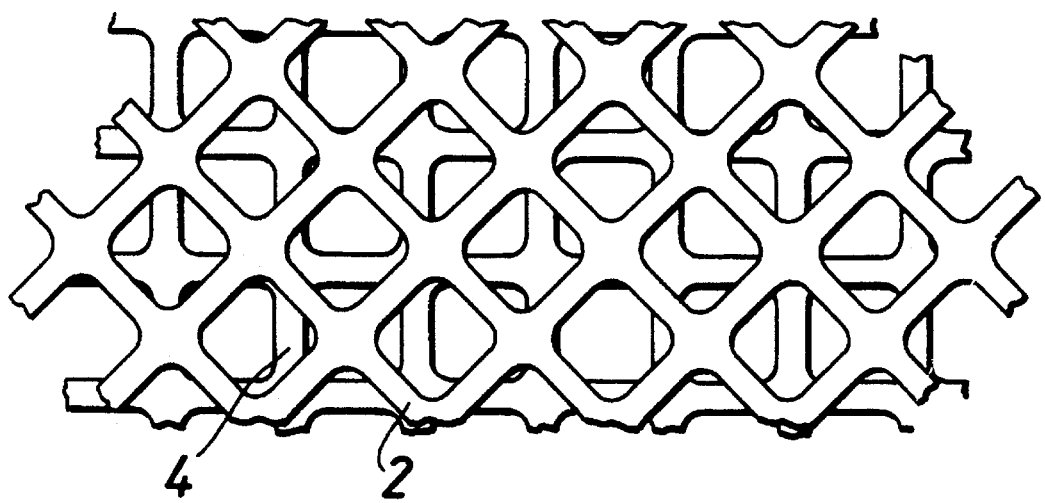
FIG. 3 is a plan view of an apertured layer employed in the present invention.

FIG. 3 illustrates two nets formed from films as hereinbefore defined. The first film or net layer 2 has a diamond pattern shape whereas the underlying film or net 4 has a square pattern. Although both films have apertures of approximately equal size it will be seen that the area of the aperture formed from the film apertures is much less than either of the areas of the apertures of the respective film.

Figure 4:
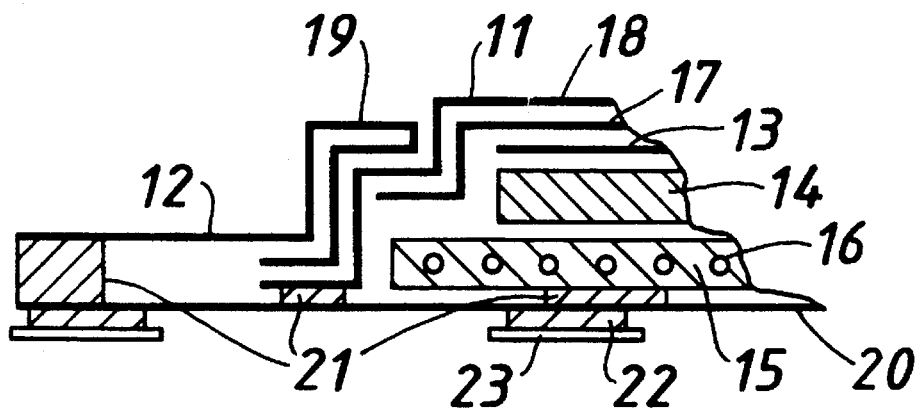
FIG. 4 is a fragmentary schematic cross-section of a 'winged' sanitary towel of the invention.

Referring to FIG. 4, the absorbent device consist of a central region 11 and a side flap or wing 12. The absorbent core formed in the central region consists of a non-woven fabric or tissue layer 13 of an upper and lower pulp bats 14 and 15 respectively. The lower bat contains particles of a super absorber material 16. Overlying the central core are an intermediate net 17 and a net cover sheet 18.

The wing section 12 is formed of a non-woven fabric 19 bonded to an extension of an impervious backing layer 20, for example formed from a polyethylene film. The liquid pervious layer is bonded to the central region and using components by, for example a hot melt adhesive 21.

The absorbent device may be affixed to a garment by adhesive strips 22 after removal of the protector tabs 23.

The invention will now be illustrated by the following example.

EXAMPLE 1

A medium size (25 cm×6.5 cm) planar elongate sanitary towel with rounded ends and a construction similar to that of FIG. 1 was formed a conventional towel forming process. The towel had an absorbent core (22 cm×6.5 cm) of tissue wrapped wood pulp (weight 9 g) enclosed within a cover sheet of polymer net. The cover sheet had an overlap on the non-body facing side of the absorbent core and also extended beyond the ends thereof where it was peripherally heat sealed.

The towel had an apertured perforated film located between the core and the cover sheet and covering the body facing surface of the core.

The towel had a barrier film (20 μm thick polyethylene film) located between the core and the sheet which covered the non-body facing surface and side edges of the core and four narrow strips of pressure sensitive adhesive located centrally on the overlap of the cover sheet which were covered by a removable protector sheet. The strips of adhesive were applied in a fluid state (hot melt) to the cover sheet so that strip impregnated and sealed overlap. The polymer net used for the cover sheet was Net 2000 Ref. LET6H27 available from Smith & Nephew Plastics Ltd.

The net had an open area in the region of 40% provided by a plurality of oval holes having an average size of 0.9 mm×0.7 mm. The apertured film used for the intermediate layer was a perforated polyethylene terephthalate film (12 μm thick) with an open area in the region of 19% provided by a plurality of oval holes having an average size of 0.5 mm×0.3 mm.

Sanitary towels prepared according to Example 1 were subjected to a fluid wet-back test and fluid absorption test.

Fluid Wet-back Test

This test measures the amount of fluid that is forced out of an absorbent device when a force of 10kPa (kilopascals) is applied to the centre of the test area.

Sanitary towels prepared according to Example 1 were subjected to a fluid wet-back test which is designed of devices having a width of at least 5.0 cm and was carried out in the following manner.

A 2.375 Kg flat weight (diameter—5.5 cm) was placed on the napkin and allowed to remain in place for 2 minutes and then removed. 5 ml of 1% saline solution coloured with lissamine green dye was delivered onto the centre of the body facing surface of the absorptive device by means of a syringe pump at a rate of 1 ml/min and at a height of 1 cm above the surface. The towel was then left to condition for 30 seconds. A pre-weighed stack of filter papers were then placed over the wetted area of the towel and the weight placed on the filter papers. For determining the absolute wet-back value filter papers are used having a mass weight of from 80–100 gm/m$^2$, typically about 90 gm/m$^2$, a thickness of from 158–212 μm @ 53KPa, typically about 185 μm; an air porosity (GURLEY) of from 5–13 sec (300 mls/in$^2$), typically about 9 sec; dry and wet burst pressures of at least 5.0 and 15.0 psi respectively and a water absorbency of about 15 mg/cm$^2$. Suitable filter papers for use in determining absolute wet-back are those sold under the trade name Whatman No. 54. The number of filter papers used should be sufficient such that top paper is not stained by the dye. After 1 minute, the filter papers were removed and weighed. The wet-back expressed as grams of fluid was then calculated from the difference in weight of the filter papers before and after compression against the absorbent device. The results are the average of tests in five samples.

Relative Optical Brightness

This test prepares the brightness of a area of surface to which fluid has been applied with that of an area to which no fluid has been applied, utilising a Lovibond Tintometer available from The Tintometer Ltd, Salisbury, England.

The relative optical brightness is determined from the following calculation.

$$\frac{\% \text{ Brightness of Area to which fluid has been applied}}{\% \text{ Brightness of Area to which no fluid has been applied}}$$

The device to be tested is conditioned for two minutes with a 1.17 kg (14cm×4.7 cm) weight placed centrally on it. 5 mls of 1% saline, containing 0.5 g/l of Fuschin Acid Stain is then dropped on the centre of the device over a period of approximately 15 seconds and at a height of about 1 cm above the device.

The test article is then left for a period of one minute for the fluid to settle. A visual brightness test of the non-wetted area of the device is made using the Tintometer.

Immediately following this, a brightness/colour test is then made on the wetted area.

A colour match is then made using the red colour dial followed by a second assessment of brightness using the visual brightness dial.

The recordings are then made as:

Visual brightness on non-wetted area.

Visual brightness on the wetted area.

Red Lovibond dial reading on the wetted area.

Calculations (a) A non-wetted area % brightness is obtained from the instrument dial reading of the Tintometer and then calculated from the Brightness reading to visual density graph which is then converted to % Brightness using the table for converting visual density to % Brightness and as described by Lovibond using the zero at 50 scale.

(b) The wetted area has two readings, the first a visual brightness dial reading a visual density reading is then obtained and added to the calculated figure from the Lovibond scale calculation, i.e.; from the renotated Lovibond colour scale. The two figures, when added together, are then converted to % Brightness using the table for converting visual density to % Brightness. The preferred graph for the conversion of the red colour source is from the Yellow at zero, and using the red value.

(c) A ratio is then obtained from the above readings of the % Brightness of the fluid impregnated surface divided by the % Brightness of the untested surface.

Sanitary towels prepared according to Example 1 were tested in comparison with two conventional commercially available sanitary towels (C1, C2) which had a similar construction to that of Example 1 except that the towels had no intermediate apertured layer and the cover sheet thereof was made of a hydrophobic fibrous non-woven fabric and (C3) an absorbent device having only one net layer over the core.

The test results were as follows:

| Sanitary Towel | Absolute Wet-back (g) | Relative Wet-back | Relative Optical Brightness |
| --- | --- | --- | --- |
| Example 1 | 0.01 | 260 | 0.66 |
| C1 | 1.9 | — | 0.48 |
| C2 | 1.3 | — | 0.39 |
| C3 | 2.6 | — | 0.61 |

The test results show that the sanitary towels of the invention exhibit a much lower wet back value than that of conventional commercially available sanitary towels.

EXAMPLES 2–7

A base polymer comprising 25 parts by weight of an ethylene-vinyl acetate copolymer (18% vinyl acetate), 59 parts by weight linear low density polyethylene, 13 parts by weight high impact polystyrene and 3% by weight titanium dioxide was divided into two portions and one portion blended with 0.6% by weight lauric diethanol amide surfactant. Each of the final blends were used to make two nets, having square and diamond shaped apertures, respectively, by— extruding the blend through an embossing roller, heating and stretching the embossed film. The apertures of the net having diamond shaped apertures were 0.66 mm long by 0.35 mm wide whereas the apertures of the net having square shaped apertures were 0.6 mm square. Hereinafter the following abbreviations will be used for the nets:

| Net Description | Abbreviation |
| --- | --- |
| Square Apertures - Surfactant Treated | ST |
| Square Apertures - No Surfactant | SU |
| Diamond Apertures - Surfactant Treated | DT |
| Diamond Apertures - No Surfactant | DU |

An hygienic absorbent device in the form of a sanitary towel was made as follows in which the body contacting apertured layer in accordance with the invention is formed of two nets wherein the body contacting net is termed the 'upper net'.

In control devices the apertured layer comprises a single apertured net.

In the manufacture of the sanitary towel, an absorbent core (216 mm long by 60 mm wide) of comminuted fluff pulp and having a central layer insert of folded tissue wadding in place centrally into the lower net of the absorbent layer. A liquid impervious film of polyethylene was then placed over the other side of the absorbent core and heat sealed around its edges to the upper net so that the lower net and the absorbent core are sandwiched between the bonding film and upper net. A portion of the exposed surface of the polyethylene backing film is provided with a pressure sensitive adhesive layer, covered by a release paper, to enable the towel to be secured to a garment.

Each of the towels was subjected to a wet-back test as described in Example 1 and the results reported in the following table:

| Example | Upper Net | Lower Net | Wet-back Value | ROB* |
| --- | --- | --- | --- | --- |
| 2 | DT | SU | 0.04 | 0.84 |
| 3 | DT | DU | 0.03 | 0.79 |
| 4 | SU | DT | 0.09 | 0.83 |
| 5 | DU | DT | 0.4 | 0.82 |
| 6 | DU | ST | 0.04 | 0.80 |
| 7 | ST | DT | 0.03 | 0.86 |
| Control 1 | DT | — | 1.67 | 0.70 |
| Control 2 | DU | — | 2.26 | 0.61 |
| Control 3 | SU | — | 1.97 | 0.65 |

*Relative optical Brightness

EXAMPLES 8–11

A surfactant treated net was produced by co-extruding two polymer blends to form an embossed film which is then heated and stretched to form a net in which the surfactant is present on one of the surfaces. The apertures were diamond-shaped, 0.56 mm long by 0.38 mm and the net mass weight was 30 gm/m².

The composition of the two polymer blends were:

| (i) | Linear Low Density Polyethylene | 60 parts by weight |
| --- | --- | --- |
| | Ethylene Vinyl Acetate (18% VA) Copolymer | 24 parts by weight |
| | High Impact Polystyrene | 12 parts by weight |
| | Titanium Dioxide | 6 parts by weight |
| (ii) | Linear Low Density Polyethylene | 40 parts by weight |
| | Ethylene Vinyl Acetate (18% VA) Copolymer | 34 parts by weight |
| | High Impact Polystyrene | 17 parts by weight |
| | Titanium Dioxide | 8 parts by weight |
| | Lauric Dietholamine amide | 1 part by weight |

The ratio of (i) to (ii) was 4:1.

Sanitary towels were made in accordance with the procedure of Examples 2 to 6 using such coextruded nets. Nets in which the surfactant treated side faces the body are termed 'Net A' whereas those in which the surfactant side faces towards the absorbent pad are termed 'Net B'. The formed sanitary towels were tested for wet-back values the results are reported as follows:

| Example | Upper Net | Lower Net | Absolute Wet-back Value | Relative Wet-back Value |
| --- | --- | --- | --- | --- |
| Control 4 | A | — | 3.08 | |
| Control 5 | B | — | 1.93 | |
| 8 | DT | A | 0.01 | 308 |
| 9 | A | DT | 0.03 | 103 |
| 10 | DT | B | 0.15 | 13 |
| 11 | B | DT | 0.8 | 2.5 |

EXAMPLES 11–12

A 'shaped' towel was produced as described in Examples 2–6 except that the absorbent core was shaped such that the central region was thicker than either the ends or the sides thereof and the non-body facing surface of the absorbent was substantially planar. The apertured body contacting layer was formed of three component nets. The wet-back volumes for nets of this construction are given in the following table:

| Example | Upper Net | Intermediate Net | Lower Net | Wet Back |
| --- | --- | --- | --- | --- |
| 12 | DT | SU | DT | 0.04 |
| 13 | SU | DT | SU | 0.02 |

The relative optical brightness for the towels were 0.90 and 0.91, respectively.

EXAMPLES 14–16

Sanitary towels were produced in accordance with the procedure described under Examples 2–7 using ethylene-vinyl acetate copolymer/linear low density polyethylene/ high input polystyrene nets (DT) in combination with as an aperture film the top of the material described as a top sheet in U.K. Patent No. 1526778 and designated P1.

The combinations of layers shown in the following table when formed into an absorbent device had the wet-back and relative optical brightness values also shown in the table.

| Example | Upper Layer | Lower Layer | Wet-Back Value (g) | Relative Optical Brightness |
| --- | --- | --- | --- | --- |
| Control 6 | DT | — | 1.79 | 0.61 |
| Control 7 | P1 | — | 0.16 | 0.62 |
| 14 | P1 | DT | 0.11 | 0.69 |

-continued

| Example | Upper Layer | Lower Layer | Wet-Back Value (g) | Relative Optical Brightness |
|---|---|---|---|---|
| 15 | P1 | P1 | ND* | 0.72 |
| 16 | DT | P1 | ND* | 0.79 |

*Not detectable.

EXAMPLE 17

Winged sanitary towels were produced having the construction shown in FIG. 4 and in accordance with the procedure and materials described for examples 2 to 7.

Example 17 incorporated a diamond upper untreated net together with a surfactant treated lower square net whilst, in the control sample, the lower square net was omitted from the construction.

The results for wet-back and relative brightness are given in the following table.

| Example | Upper Layer | Lower Layer | Wet-Back Value (g) | Relative Optical Brightness |
|---|---|---|---|---|
| 17 | DU | ST | 0.06 | 0.80 |
| Control 8 | DU | — | 1.44 | 0.61 |

I claim:

1. An absorbent device having low fluid wet-back, comprising;

an absorbent core having a body facing side;

a cover sheet on said body-facing side of said absorbent core; and an intermediate layer between said absorbent core and said cover sheet;

wherein said cover sheet comprises an apertured polymer film and said intermediate layer consists essentially of a planar apertured polymer film, and wherein said cover sheet and said intermediate layer have open areas, said open area of said cover sheet being greater than said open area of said intermediate layer.

2. An absorbent device according to claim 1, wherein at least one of said apertured polymer films is a polymer net having apertures defined by integral strands and junctions formed from the polymer material.

3. An absorbent device according to claim 1, wherein said intermediate layer contains a surfactant.

4. An absorbent device according to claim 1, having a wet-back value of not more than 0.2 g.

5. An absorbent device according to claim 4, having a wet-back value of less than 0.1 g.

6. An absorbent device according to claim 1, in the form of a sanitary napkin, diaper or tampon.

7. An absorbant device having low fluid wet-back and a high relative brightness, comprising;

an absorbent core having a body-facing side;

a body-contacting cover sheet on said body-facing side of said absorbent core, said cover sheet having a body-contacting surface; and an intermediate layer between said absorbent core and said cover sheet;

wherein said cover sheet comprises an apertured polymer film and said intermediate layer consists essentially of a planar apertured polymer film;

the optical brightness of a stained area of said body-contacting surface of said cover sheet and the optical density of an unstained area of said body-contacting surface being comparable.

8. An absorbent device according to claim 7, having a relative optical brightness of at least 0.65.

9. An absorbent device according to claim 8, having a relative optical brightness of at least 0.75.

10. An absorbent device, comprising an absorbent core having a first surface and an apertured body-facing layer covering said first surface of said absorbent core, said apertured body-facing layer comprising a layered array of two flexible substantially planar polymer nets having apertures defined by integral strands and junctures formed from the polymer material.

11. A method of producing an absorbent device having low fluid wet-back, comprising at least partially covering a body-facing surface of an absorbent core with a cover sheet and an intermediate layer, said intermediate layer being between said cover sheet and said absorbent core, wherein said cover sheet comprises an apertured polymer film and said intermediate layer consists essentially of a planar apertured polymer film.

12. A method according to claim 11, wherein each said apertured film is a flexible polymer net having apertures defined by the integral strands and junctures formed from the polymer material.

* * * * *